(12) United States Patent
Deng et al.

(10) Patent No.: US 9,387,002 B2
(45) Date of Patent: Jul. 12, 2016

(54) SURGICAL INSTRUMENT

(71) Applicants: Shanghai YAOCHUAN Information Technology CO., Ltd., Shanghai (CN); Xerafy Ltd (BVI), Tortola (VG)

(72) Inventors: Yong Deng, Sichuan (CN); Zhijia Liu, Shanghai (CN)

(73) Assignees: Shanghai Yaochuan Information Technology Co., Ltd., Shanghai (CN); Xerafy Ltd (BVI), Tortola (VG)

( * ) Notice: Subject to any disclaimer, the term of this patent is extended or adjusted under 35 U.S.C. 154(b) by 0 days.

(21) Appl. No.: 14/686,225

(22) Filed: Apr. 14, 2015

(65) Prior Publication Data

US 2015/0272690 A1   Oct. 1, 2015

Related U.S. Application Data

(63) Continuation of application No. PCT/CN2015/074134, filed on Mar. 12, 2015.

(30) Foreign Application Priority Data

Mar. 31, 2014 (CN) .......................... 2014 1 0127677

(51) Int. Cl.
*G06F 19/00* (2011.01)
*A61B 17/28* (2006.01)
*A61B 17/3201* (2006.01)

(52) U.S. Cl.
CPC .............. *A61B 17/28* (2013.01); *A61B 17/3201* (2013.01)

(58) Field of Classification Search
CPC ............ G06Q 10/087; G06Q 10/0833; G06Q 10/0875
USPC ................................ 235/385, 462.46, 472.02
See application file for complete search history.

(56) References Cited

U.S. PATENT DOCUMENTS 8,600,374 B1 * 12/2013 Hertlein .................. H04M 1/18
455/425
2006/0267167 A1 * 11/2006 McCain ............. G06K 19/0702
257/678

(Continued)

FOREIGN PATENT DOCUMENTS

CN       101172052 A    5/2008
CN       101304775 A   11/2008

(Continued)

OTHER PUBLICATIONS

International Search Report dated Jun. 29, 2015 issued in International Application No. PCT/CN2015/074134.

*Primary Examiner* — Daniel St Cyr
(74) *Attorney, Agent, or Firm* — Renner, Otto, Boisselle & Sklar, LLP

(57) ABSTRACT

The disclosure discloses a surgical instrument which comprises an instrument body and an encapsulated electronic device, wherein the instrument body is partially or completely made of a metal material; the encapsulated electronic device comprises a radio frequency identification chip which is electrically connected with the instrument body; the instrument body, which serves as an antenna of the radio frequency identification chip, is configured to acquire the electromagnetic wave energy so as to activate the radio frequency identification chip. According to the surgical instrument, the instrument body, which serves as the antenna of the encapsulated electronic device, is configured to acquire the electromagnetic wave energy so as to activate the radio frequency identification chip, so that no antenna is needed to be configured in the encapsulated electronic device, and thus the encapsulated electronic device cannot affect operations of medical staff due to small size and can achieve excellent reading effect.

10 Claims, 12 Drawing Sheets

(56) References Cited

U.S. PATENT DOCUMENTS

| | | | |
|---|---|---|---|
| 2008/0030345 A1* | 2/2008 | Austin | A61B 19/44 340/572.8 |
| 2009/0051540 A1 | 2/2009 | Fu et al. | |
| 2009/0072029 A1* | 3/2009 | Martin | G06Q 10/087 235/385 |
| 2013/0228627 A1 | 9/2013 | Chen et al. | |

FOREIGN PATENT DOCUMENTS

| | | |
|---|---|---|
| CN | 101390111 A | 3/2009 |
| CN | 102346867 A | 2/2012 |
| CN | 102496053 A | 6/2012 |
| CN | 102542326 A | 7/2012 |
| CN | 102897112 A | 1/2013 |

* cited by examiner

US 9,387,002 B2

SURGICAL INSTRUMENT

CROSS-REFERENCE TO RELATED APPLICATIONS

This application is a continuation application of PCT Application PCT/CN2015/074134, filed on Mar. 12, 2015, which claims priority to Chinese Application No. 201410127677.1, filed on Mar. 31, 2014, the contents of each of which are incorporated herein by reference.

TECHNICAL FIELD

The present disclosure relates to a surgical instrument, which is particularly related to a tracking and positioning structure of the surgical instrument.

BACKGROUND ART

With the development of RFID (Radio Frequency Identification) technology, more and more RFID application requirements are proposed, such as management of surgical instruments in the medical industry. At present, in accidents of the medical industry, most of medical accidents are derived from incomplete sterilization process of surgical instruments and loss of instruments in the patient's body. It is thereby effective to prevent similar problems from happening by adopting the RFID technology (Unique Identification) to trace and manage the surgical instruments in real time. However, due to the miniaturized and integrated technical restriction of the current RFID tag technology, how to additionally configure RFID tags on the surgical instruments becomes considerable difficulty and challenge. The current RFID tag mainly consists of an RFID chip, a tag antenna and an encapsulating material. The RFID tag is mainly configured on the surface of the surgical instrument or tool in the using process, thus realizing tracking and managing of tools and surgical instruments. The RFID tag, due to arrangement of the antenna, causes relatively large size and poor reading performance, and needs to be fitted on the surface of the surgical instrument or embedded to the surgical instrument in the way of the connecting mode. The surgical instrument on which the tag is fitted in a traditional manner always causes inconvenience to clinical operations of doctors and is thus easy to lose.

SUMMARY

The present disclosure is embodied by the follow technical solution:

A surgical instrument comprises an instrument body and an encapsulated electronic device, wherein the instrument body is partially or completely made of a metal material, the encapsulated electronic device comprises a radio frequency identification chip which is electrically connected with the instrument body, and the instrument body, which serves as an antenna of the radio frequency identification chip, is configured to acquire the electromagnetic wave energy activate the radio frequency identification chip.

Further, the radio frequency identification chip is electrically connected with the instrument body through a parallel or series matching network, and the matching network is configured to adjust the impedance change of the instrument body to form conjugate match of impedance with the radio frequency identification chip so as to achieve the maximum transmission of power.

Further, the radio frequency identification chip, the matching network and the instrument body are electrically connected through a transmission line feed network.

Further, the encapsulated electronic device is filled with an encapsulating material which is configured to encapsulate the radio frequency identification chip, the matching network and the transmission line feed network therein.

Further, the encapsulating material is a biocompatible material according with implantation standards.

Further, the encapsulated electronic device constitutes a part of the structure of the instrument body.

Further, connecting parts are configured at two ends of the encapsulated electronic device, and the encapsulated electronic device is connected with the instrument body into a whole through the connecting parts.

Further, the connecting part comprises a stainless steel solder pad which is welded with the instrument body.

Further, the connecting part comprises a stainless steel clamping structure, wherein a structure matched with the stainless steel clamping structure is correspondingly configured on the instrument body and the stainless steel clamping structure is welded with the instrument body after clamping.

Further, a tenon is configured on the end part of the stainless steel clamping structure and is matched with a groove which is correspondingly configured in the instrument body.

BRIEF DESCRIPTION OF THE DRAWINGS

The present disclosure will be described in further detail in conjunction with accompanying drawings below.

DETAILED DESCRIPTIONS OF THE EMBODIMENTS

Exemplary embodiments embodying features and advantages of the present disclosure will be described in detail in the following description. It should be understood that the present disclosure can have various variations, which neither departing from the scope of the disclosure, and description and drawings are essentially as illustrative and not intended to limit the present disclosure.

Figure 1:
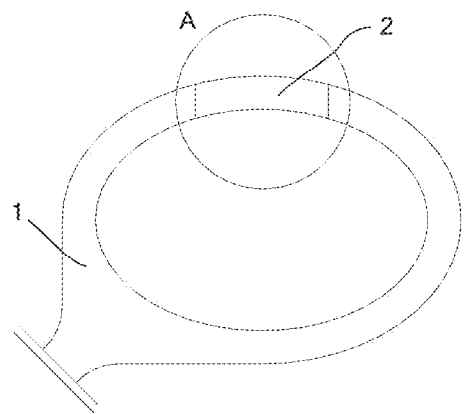
FIG. 1 is the first kind of structure schematic diagram of the surgical instrument of the present disclosure.

As shown in FIG. 1, a surgical instrument of the present disclosure comprises an instrument body 1 and an encapsulated electronic device 2. The instrument body 1 is partially or completely made of a metal material, so that the instrument body 1 can serve as an antenna of the encapsulated electronic device 2. The instrument body 1 can be a surgical apparatus, such as haemostatic forceps or surgical scissors; the encapsulated electronic device 2 acting as a part structure member of the instrument body 1 constitutes the surgical instrument together with the instrument body 1, rather than being configured independently. In the actual manufacturing process, a part of a handle part of the instrument body 1 can also be removed, and subsequentially, the encapsulated electronic device 2 is made into a style which is the same as the shape structure of the removed part, and is connected with the instrument body 1 into a whole. In addition, the encapsulated electronic device 2 can also be embedded and welded to the main body part of the instrument body 1 in case of not affecting the strength of the instrument body 1; and the mounting position of the encapsulated electronic device 2 is not limited to the structure in this embodiment as long as said functions of the present disclosure are achieved.

Figure 2:
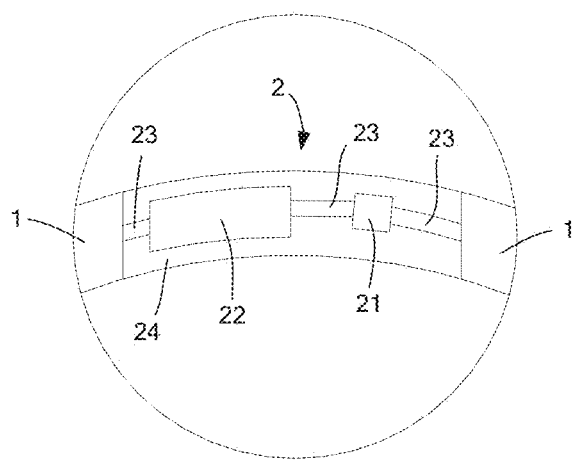
FIG. 2 is a structure schematic diagram of an amplified part A in FIG. 1 (Tandem structure)
Figure 3:
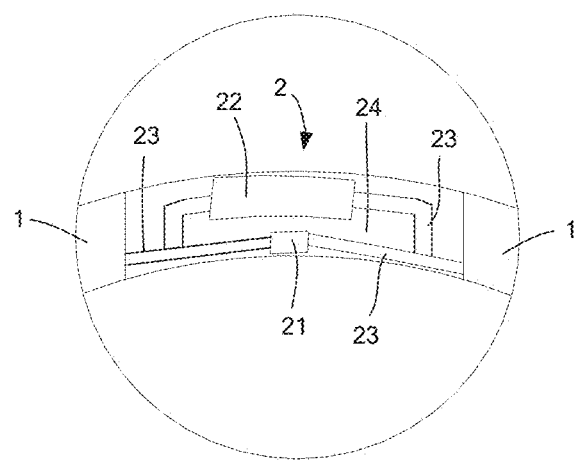
FIG. 3 is a structure schematic diagram of an amplified part A in FIG. 1 (Parallel structure)

As shown in FIG. 2 and FIG. 3, in the present disclosure, the encapsulated electronic device 2 comprises a radio frequency identification chip 21, a matching network 22, a transmission line feed network 23 and an encapsulating material 24, wherein the radio frequency identification chip 21 is electrically connected with the instrument body 1, and the instrument body 1, which serves as an antenna of the radio frequency identification chip 21, is configured to acquire the electromagnetic wave energy so as to activate the radio frequency identification chip 21. In this embodiment, the radio frequency identification chip 21 is electrically connected with the instrument body 1 through a parallel of series matching network 22 (FIG. 2 refers to the series structure and FIG. 3 refers to the parallel structure); the matching network 22 is configured to adjust the impedance change caused by changes of size and the like to form conjugate match of impedance with the radio frequency identification chip 21 so as to achieve maximum transmission of power. In this embodiment, the radio frequency identification chip 21, the matching network 22 and the instrument body 1 are electrically connected through the transmission line feed network 23. In this embodiment, the encapsulated electronic device is filled with the encapsulating material 24 which is configured to encapsulate the radio frequency identification chip 21, the matching network 22 and the transmission line feed network 23 therein, and the encapsulating material 24 is a biocompatible material according with implementation standards and is free of any repellence and adverse reactions when contacting the human body. In the present disclosure, the encapsulating material 24 needs to reach an IP69 waterproof level and can be subjected to sterilization procedures, such as medical high temperature disinfection. Therefore, the encapsulating material 24 can effectively protect the encapsulated electronic device 2 against the influences of the surgical instrument during high temperature steam sterilization, ultraviolet irradiation and cleaning process.

In the present disclosure, connecting parts are configured at two ends of the encapsulated electronic device 2, and the encapsulated electronic device 2 is connected with the instrument body 1 into a whole through the connecting parts. The structure of the connecting parts is not limited, and the following two examples are proposed in order to illustrate the exploitativeness of the structure: firstly, the connecting part comprises a stainless steel solder pad which is welded with the instrument body 1; and secondly, the connecting part comprises a stainless steel clamping structure, and a structure matched with the stainless steel clamping structure is correspondingly configured on the instrument body 1, wherein the stainless steel clamping structure is welded with the instrument body 1 after clamping, and a tenon is configured on the end part of the stainless steel clamping structure and is matched with a groove which is correspondingly configured in the instrument body 1.

In the present disclosure, the encapsulated electronic device 2 only works when mounted on the instrument body 1 (since the encapsulated electronic device 2 does not have an antenna per se and thus cannot work after being disassembled in the absence of antenna), however, the radio frequency identification chip 21 cannot be read once the encapsulated electronic device is disassembled, and by means of the structure, the fake and poor quality commodities are effectively prevented from appearing. When old surgical instruments are obsoleted, the encapsulated electronic device 2 is obsoleted along with the instrument body 1 rather than being recycled.

Compared with the existing technology, the present disclosure lies in that: the instrument body, which serves as the antenna of the encapsulated electronic device, is configured to acquire the electromagnetic wave energy so as to activate the radio frequency identification chip, so that no antenna is needed to be configured in the encapsulated electronic device, and thus the present disclosure cannot affect the operations of medical staff due to small size and achieves a very good reading effect.

Furthermore, the present disclosure has the advantages of small size, high integration level and good performances and realizes complete integration with the surgical instruments; the present disclosure effectively expands the available area and size of the antenna and greatly improves the readability of the radio frequency identification chip 21; in addition, the matching network 22 can perform more flexible adjustment so as to match with frequency shift and impedance change problems caused by different sizes of instrument bodies 1; the surgical instrument claimed in the present disclosure has no any difference with standard surgical instruments in aspects of appearance and use, without any adverse effect on normal use thereof, thus reducing the misoperations and being safer and more reliable.

Figure 4:
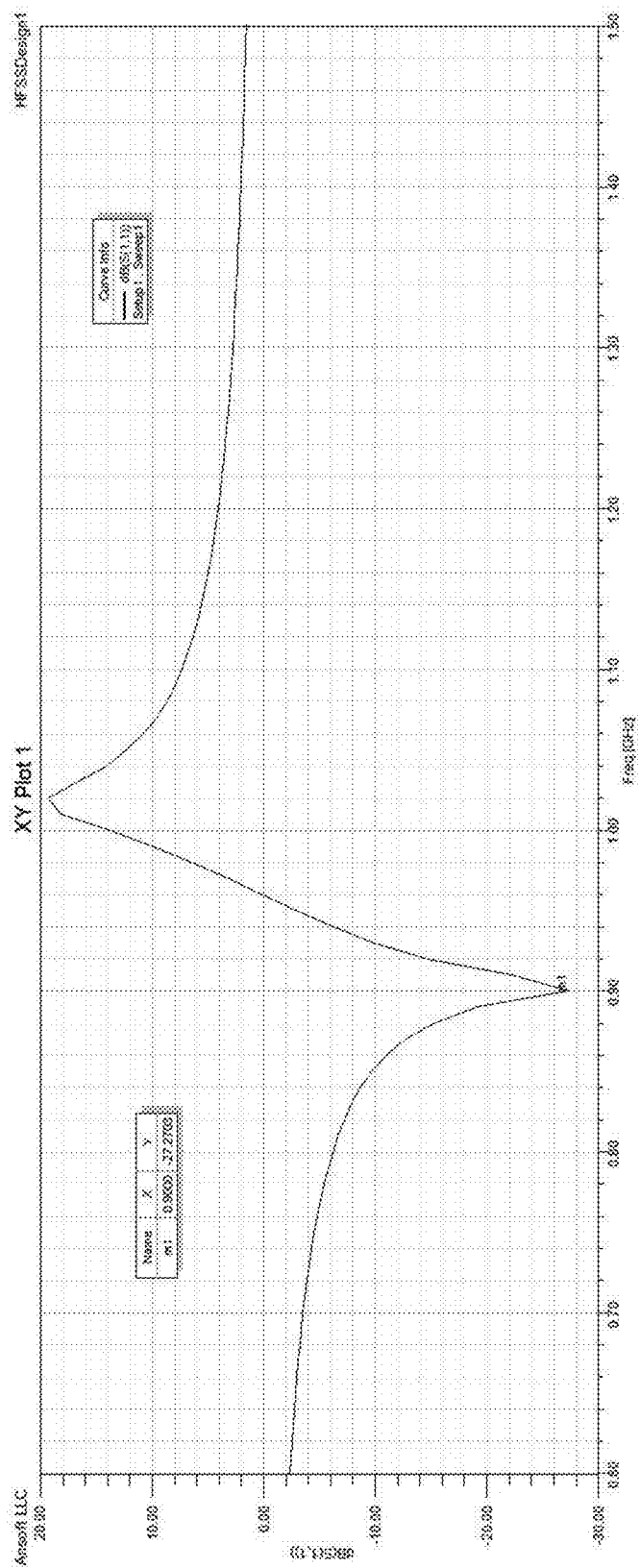
FIG. 4 is an effect diagram of a parameter S11 curve of the existing technology.
Figure 5:
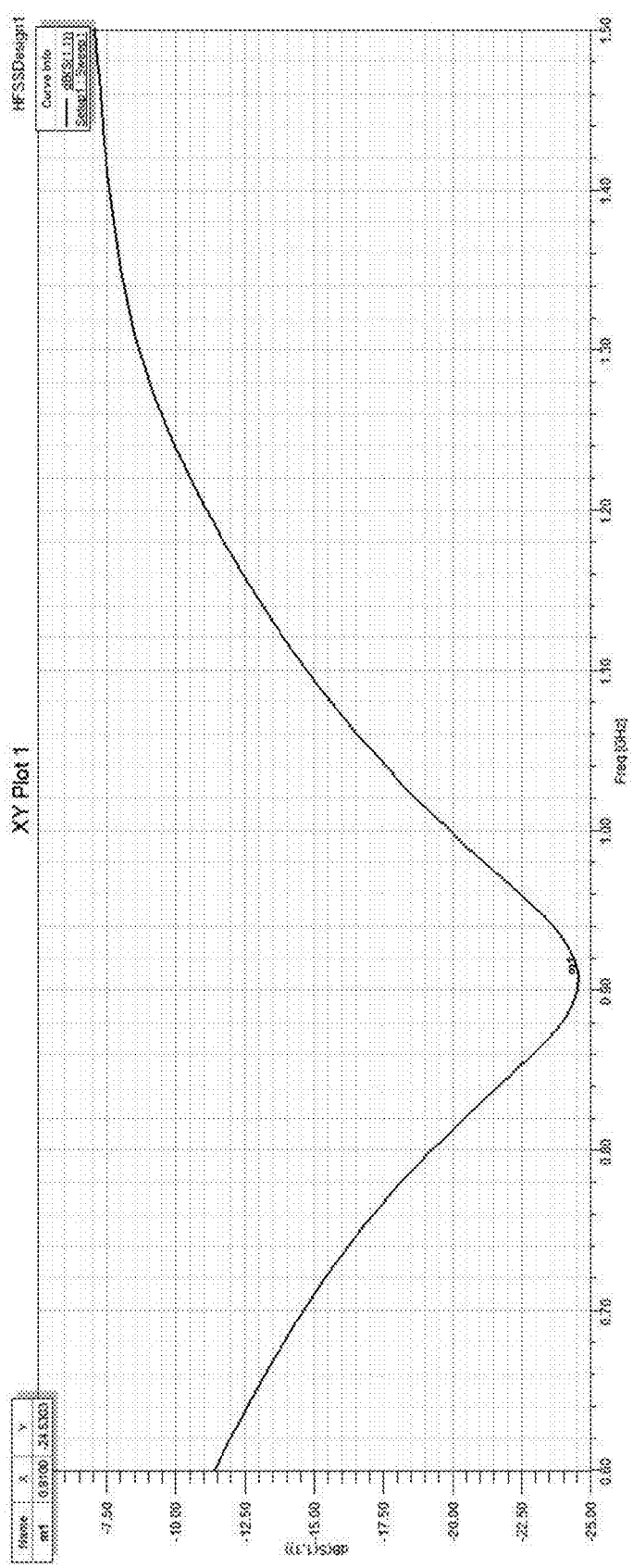
FIG. 5 is an effect diagram of the parameter S11 curve of the present disclosure.

As for the performances of the present disclosure, simulation argument is performed. Said simulation comprises a parameter S11 (a port reflection parameter mainly reflecting the matching degree between source impedance and load impedance, wherein a lower value means higher matching degree, and it is generally recognized that −15 dBm is a basic impedance matching value.) curve comparison, an antenna gain diagram and an impedance parameter curve diagram. Wherein, FIG. 4 and FIG. 5 show comparison diagrams of parameter S11 curves of the present disclosure and the existing technology, wherein FIG. 5 is a parameter S11 curve of the present disclosure, and FIG. 4 is a parameter S11 curve of the existing technology. In the present disclosure, the resonant frequency is 910 MHz, and the minimum value of the parameter S11 is −24.5 dB. The bandwidth less than −15 dB ranges from 700 MHz and 1.1 GHz, totaling in 400 MHz bandwidth, and completely covers all UHF ultrahigh-frequency RFID frequency bands (860-960 MHz). In the existing technology, the resonant frequency is 900 MHz, and the minimum value of S11 is −27 dB, wherein the frequency range of S11 value less than −15 dB is from 880 MHz to 920 MHz, about 40 MHz bandwidth, which causes difficulty of realizing global coverage of RFID frequency band.

Figure 6:
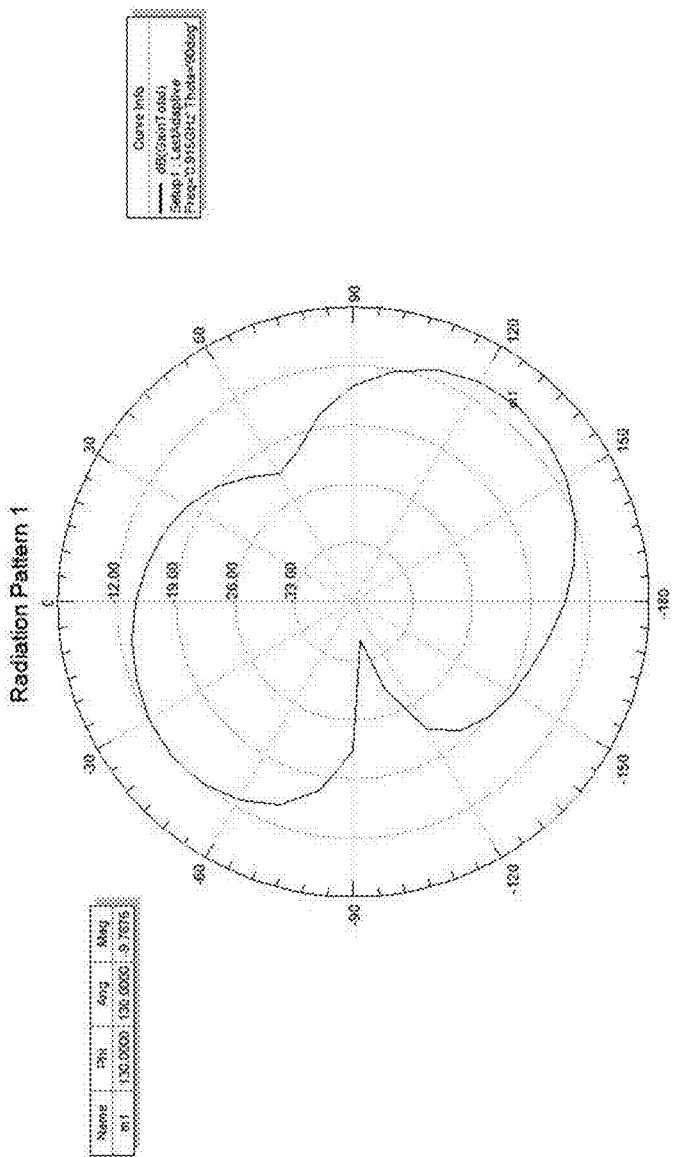
FIG. 6 is an effect diagram of antenna gain of the existing technology.
Figure 7:
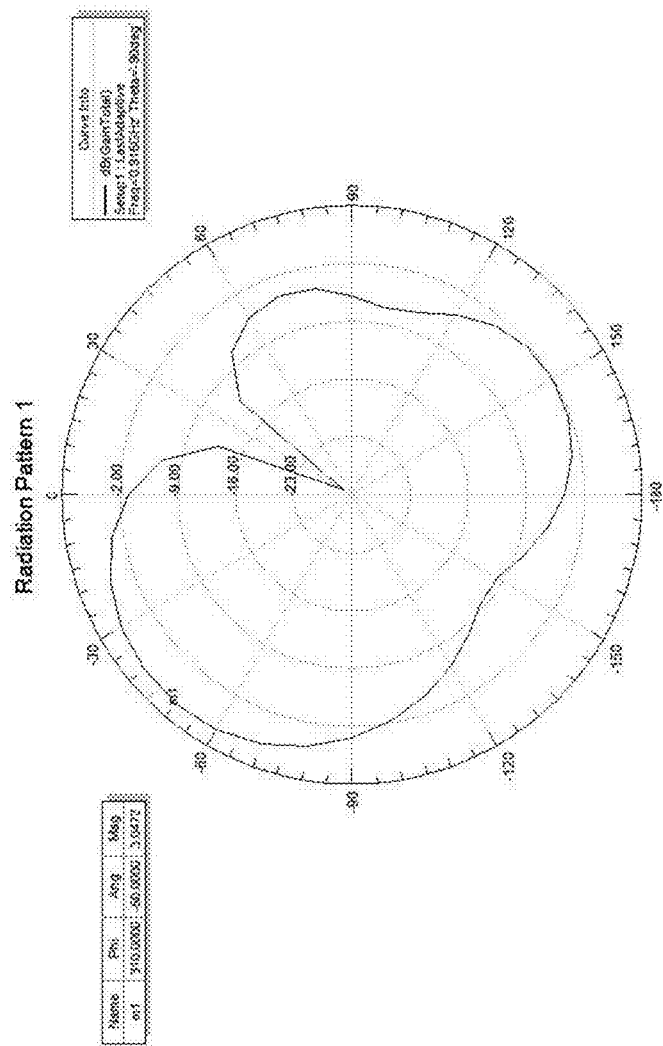
FIG. 7 is an effect diagram of antenna gain of the present disclosure.
Figure 8:
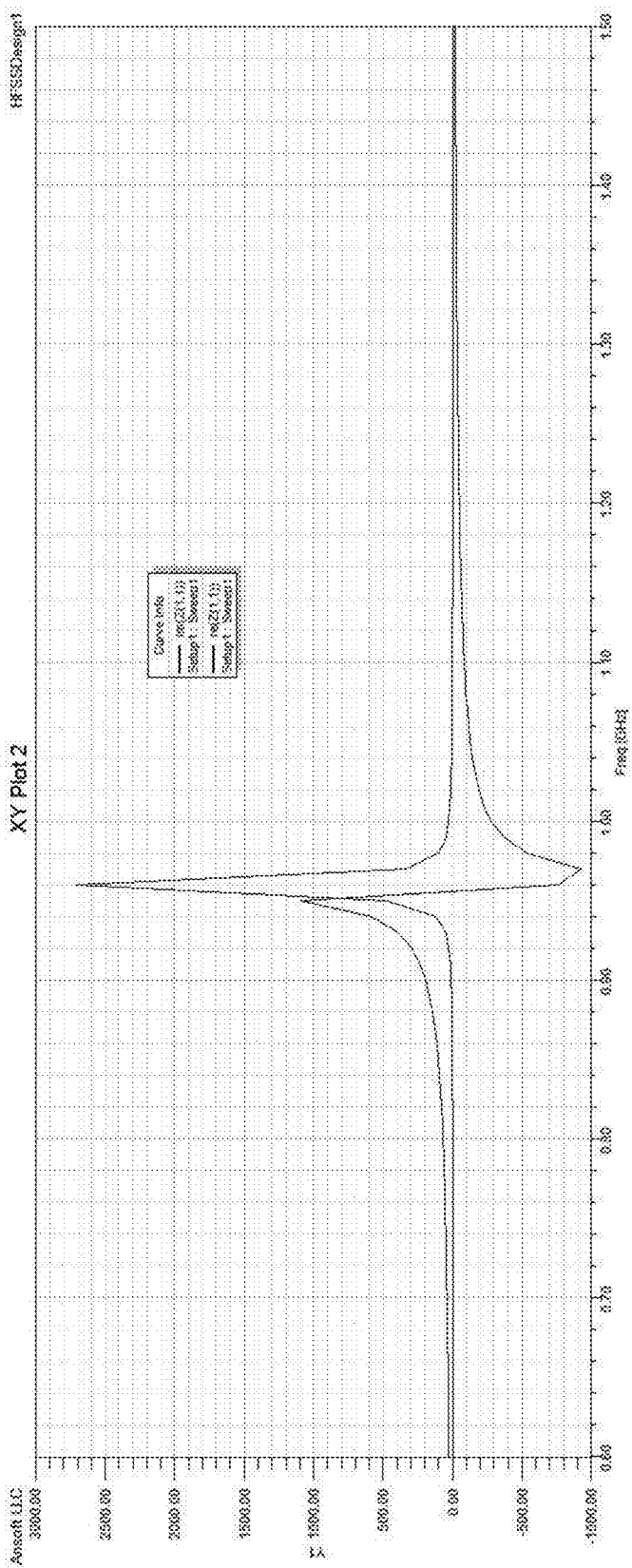
FIG. 8 is an effect diagram of the impedance parameter curve of the existing technology.
Figure 9:
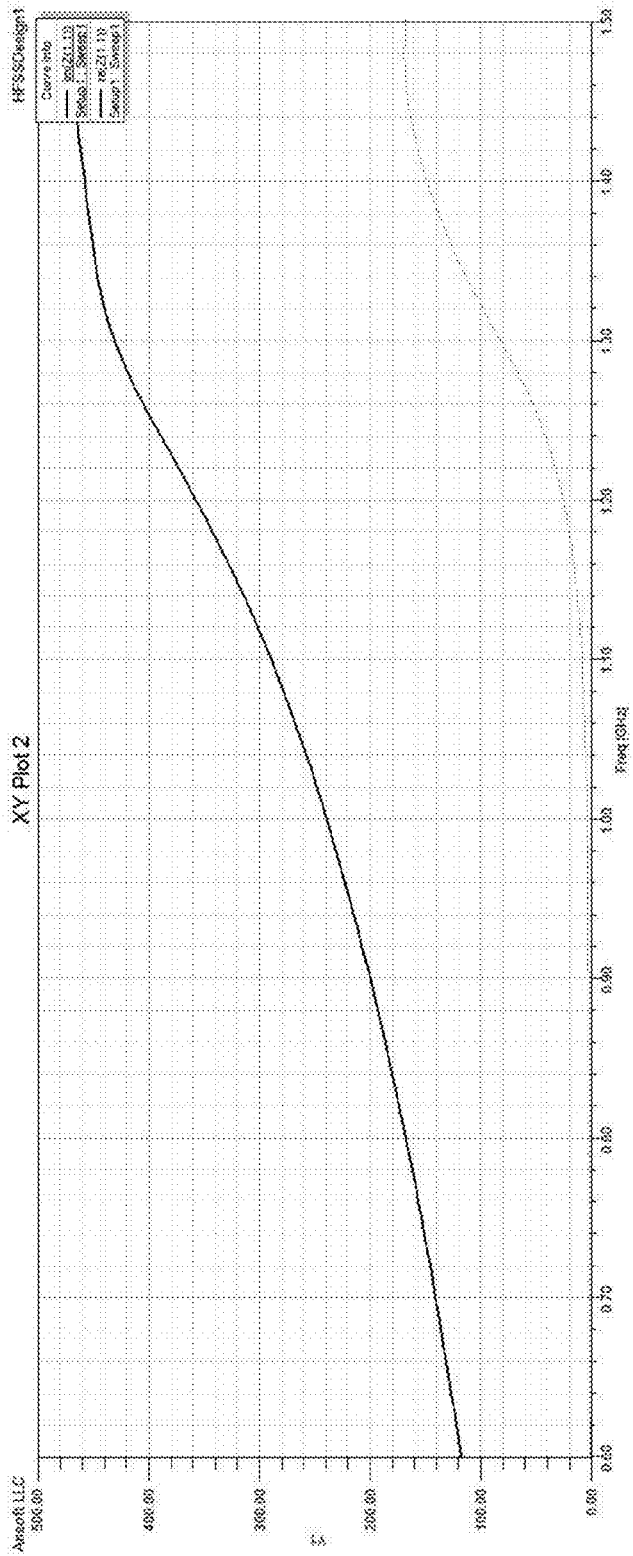
FIG. 9 is an effect diagram of the impedance parameter curve of the present disclosure.
Figure 10:
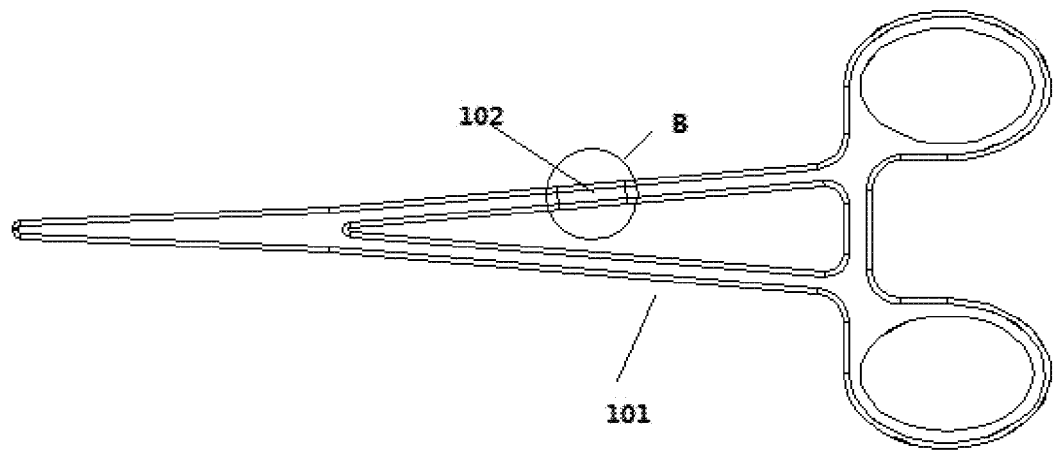
FIG. 10 is the second kind of structure schematic diagram of the surgical instrument of the present disclosure.

FIG. 6 and FIG. 7 show the comparison diagrams of antenna gains of the present disclosure and the existing technology, wherein FIG. 7 is antenna gain of the present disclosure and FIG. 6 is antenna gain of the existing technology. In the present disclosure, when the structure is at 915 MHz and Theta=90°, the maximum gain is 3.04 dB. In the existing technology, when the structure is at 915 MHz and Theta=90°, the gain is only −9.8 dB, which is nearly 13 dB less than that of the present disclosure, about a fivefold difference. Finally, FIG. 8 and FIG. 9 show the comparison diagrams of the impedance parameter curves of the present disclosure and the existing technology, wherein FIG. 9 is load impedance matching degree of the present disclosure, and FIG. 8 is load impedance matching degree of the existing technology.

As shown in FIG. 10-17, a surgical instrument of the present disclosure comprises an instrument body 101,121, 141,161 and an encapsulated electronic device 102,122,142, 162. The sad instrument body is partially or completely made of a metal material, so that the instrument body can serve as an antenna of the encapsulated electronic device. The instrument body can be a surgical apparatus, such as haemostatic forceps or surgical scissors.

The encapsulated electronic device 102,122,142,162 are acting as a part structure member of the instrument body 101,121,141,161 constitutes the surgical instrument together with the instrument body 101,121,141,161 rather than being configured independently. In the actual manufacturing process, a part of the instrument body 101,121,141,161 can be removed, and subsequently, the encapsulated electronic device 102,122,142,162 are made as same as the shape structure of said removed part, and are connected with the instrument body 101,121,141,161 into a whole. In addition, the encapsulated electronic device 102,122,142,162 can also be embedded and welded to the main body part of the instrument body 101,121,141,161 in case of not affecting the strength of the instrument body 101,121,141,161; and the mounting position of the encapsulated electronic device 102,122,142, 162 is not limited to the structure in this embodiment as long as said functions of the present disclosure are achieved.

Figure 11:
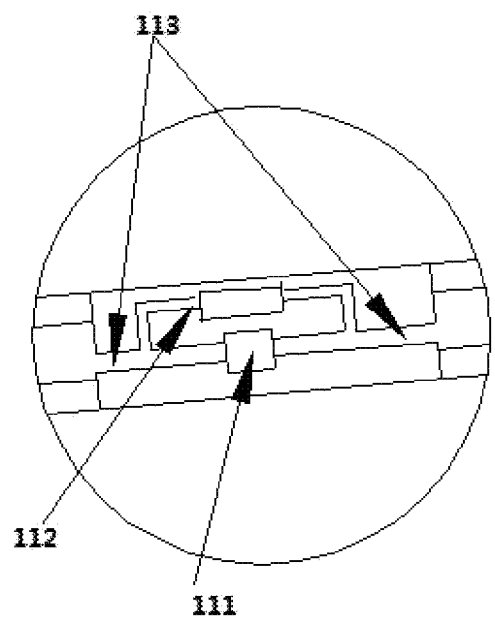
FIG. 11 is a structure schematic diagram of an amplified part B in FIG. 10.
Figure 12:
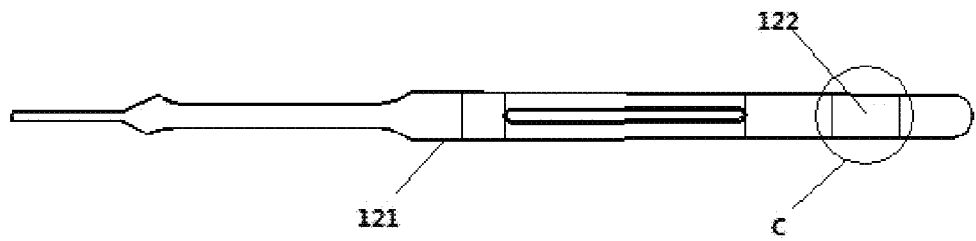
FIG. 12 is the third kind of structure schematic diagram of the surgical instrument of the present disclosure.
Figure 13:
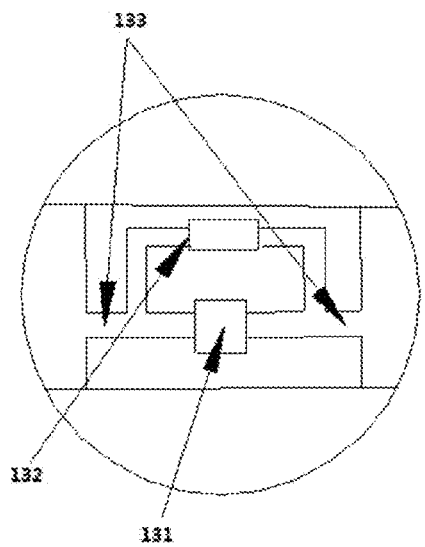
FIG. 13 is a structure schematic diagram of an amplified part C in FIG. 12.
Figure 14:
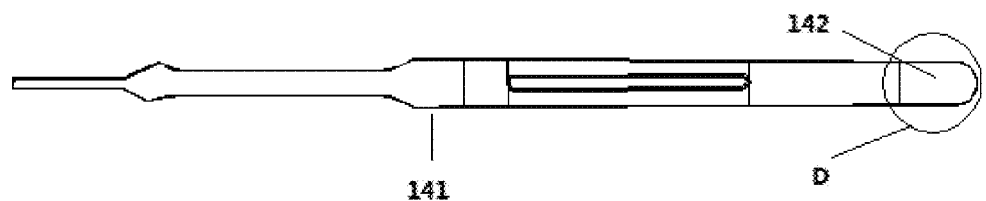
FIG. 14 is a the fourth of structure schematic diagram of the surgical instrument of the present disclosure.
Figure 15:
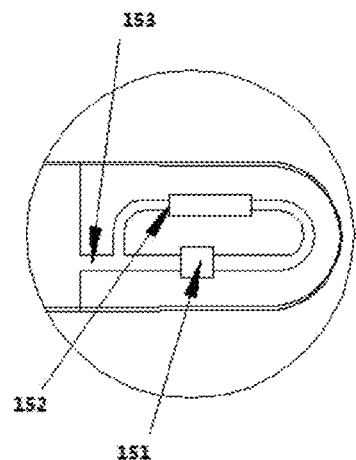
FIG. 15 is a structure schematic diagram of an amplified part D in FIG. 14.
Figure 16A:
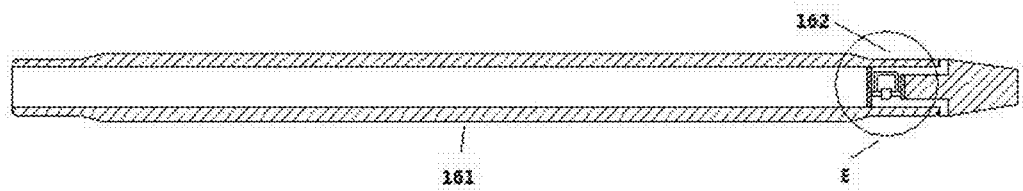
FIG. 16A and FIG. 16B are the fifth of structure schematic diagram of the surgical instrument of the present disclosure.
Figure 16B:
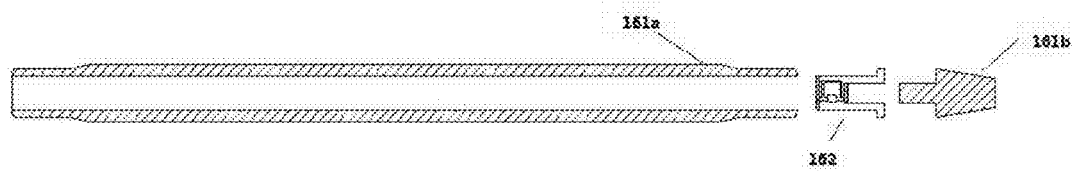
Figure 17:
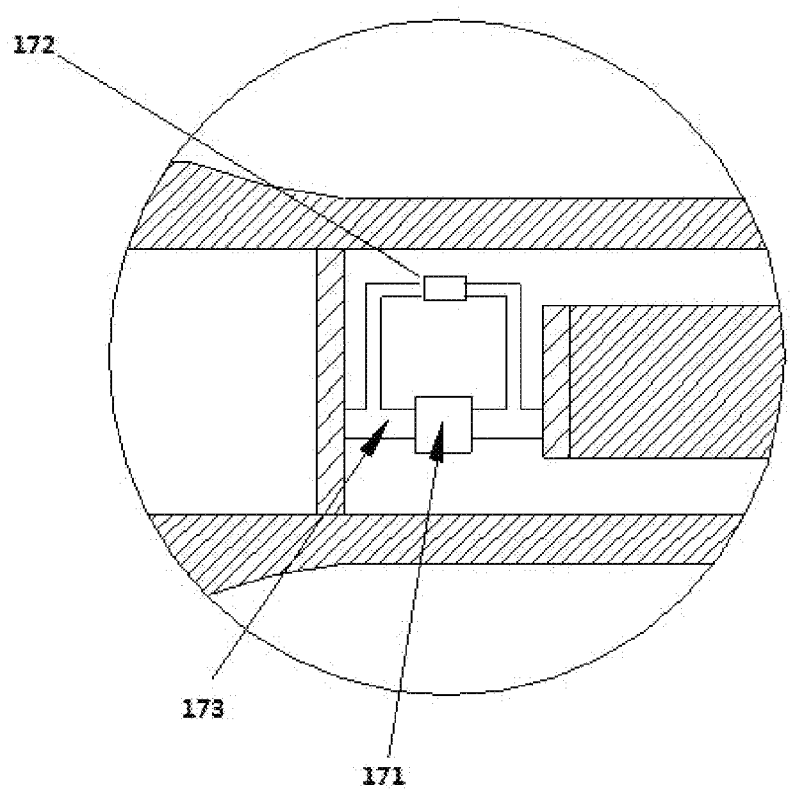
FIG. 17 is a structure schematic diagram of an amplified part E in FIG. 16A.

As shown in FIG. 11,13,15,17 in the present disclosure, the encapsulated electronic device 102,122,142 comprises a radio frequency identification chip 111,131,151,171 a matching network 112,132,152, 172, a transmission line feed network 113,133,153,173. The radio frequency identification chip 111.131.151,171 is electrically connected with the instrument body 101,121,141,161, and the instrument body 101,121,141,161 which serves as an antenna of the radio frequency identification chip 111.131.151,171 is configured to acquire the electromagnetic wave energy so as to activate the radio frequency identification chip 111.131.151,171. In these embodiments, the radio frequency identification chip 111,131,151,171 is electrically connected with the instrument body 101,121,141,161 through a parallel of series matching network 112,132,152; the matching network 112, 132,152,172 is configured to adjust the impedance change caused by changes of size and the like to form conjugate match of impedance with the radio frequency identification chip 111,131,151 so as to achieve maximum transmission of power. In these embodiments, the radio frequency identification chip 111,131,151,172, the matching network 112,132, 152,172 and the instrument body 101,121,141,161 are electrically connected through the transmission line feed network 113,133,153,173. In these embodiments, the encapsulated electronic device is filled with the encapsulating material which is configured to encapsulate the radio frequency identification chip 111,131,151,171, the matching network 112, 132,152,172,172 and the transmission line feed network 113, 133,153,173, therein, and the encapsulating material is a biocompatible material according with implementation standards and is free of any repellence and adverse reactions when contacting the human body.

In the present disclosure, the encapsulating material needs to reach an IP69 waterproof level and can be subjected to sterilization procedures, such as medical high temperature disinfection. Therefore, the encapsulating material can effectively protect the encapsulated electronic device 102,122, 142,162 against the influences of the surgical instrument during high temperature steam sterilization, ultraviolet irradiation and cleaning process.

As show in FIG. 16A and FIG. 16B, 161a and 161b are the two parts of instrument body 161. The inner wall of instrument body 161a is electrical connection with the encapsulated electronic device 162, and the undersurface of instrument body 161b is electrical connection with the encapsulated electronic device 162.

As stated above, the embodiments abovementioned of the present disclosure are described, however, those skilled in the art should recognize that both changes and variations, made without departing from the scope and sprit of the claimed disclosure as disclosed in the appended claims of the present disclosure, fall into the protection scope of the claims of the present disclosure.

The invention claimed is:

1. A surgical instrument, comprising:
an instrument body partially or completely made of a metal material; and
an encapsulated electronic device, comprising a radio frequency identification chip which is electrically connected with the instrument body,
wherein the instrument body serves as an antenna of the radio frequency identification chip to acquire electromagnetic wave energy so as to activate the radio frequency identification chip.

2. A surgical instrument according to claim 1, wherein said radio frequency identification chip is electrically connected with said instrument body through a matching network in parallel or in series, and the matching network adjusts impedance change of said instrument body to form conjugate match of impedance with said radio frequency identification chip so as to achieve maximum transmission of power.

3. A surgical instrument according to claim 2, wherein said radio frequency identification chip, said matching network and said instrument body are electrically connected through a transmission line feed network.

4. A surgical instrument according to claim 3, wherein said encapsulated electronic device is filled with an encapsulating material which encapsulates said radio frequency identification chip, said matching network and said transmission line feed network therein.

5. A surgical instrument according to claim 4, wherein said encapsulating material is a biocompatible material according with implantation standards.

6. A surgical instrument according to claim 5, wherein said encapsulated electronic device constitutes a part of the structure of said instrument body.

7. A surgical instrument according to claim 6, wherein connecting parts are disposed at two ends of the encapsulated electronic device, and the encapsulated electronic device and the instrument body are connected into a whole by virtue of the connecting parts.

8. A surgical instrument according to claim 7, wherein said connecting part comprises a stainless steel solder pad which is welded with the instrument body.

9. A surgical instrument according to 7, wherein said connecting part comprises a stainless steel clamping structure, wherein a structure matched with the stainless steel clamping structure is correspondingly disposed on the instrument body, and said stainless steel clamping structure is welded with said instrument body after clamping.

10. A surgical instrument according to claim 9, wherein a tenon is disposed at an end part of said stainless steel clamping structure and matched with a groove correspondingly disposed in the instrument body.

* * * * *